(12) United States Patent
Zhao et al.

(10) Patent No.: US 11,504,553 B2
(45) Date of Patent: Nov. 22, 2022

(54) RADIATION THERAPY DEVICE AND SYSTEM

(71) Applicants: OUR UNITED CORPORATION, Xi'an (CN); Shenzhen OUR New Medical Technologies Development Co., Ltd., Shenzhen (CN)

(72) Inventors: Hongbin Zhao, Xi'an (CN); Haifeng Liu, Xi'an (CN); Ming Zhong, Xi'an (CN); Huiliang Wang, Xi'an (CN)

(73) Assignees: OUR UNITED CORPORATION, Xi'an (CN); Shenzhen OUR New Medical Technologies Development Co., Ltd., Shenzhen (CN)

( * ) Notice: Subject to any disclaimer, the term of this patent is extended or adjusted under 35 U.S.C. 154(b) by 0 days.

(21) Appl. No.: 16/927,334

(22) Filed: Jul. 13, 2020

(65) Prior Publication Data

US 2020/0338369 A1  Oct. 29, 2020

Related U.S. Application Data

(63) Continuation of application No. PCT/CN2019/070849, filed on Jan. 8, 2019.

(30) Foreign Application Priority Data

Jan. 15, 2018  (CN) .......................... 201810037191.7

(51) Int. Cl.
*A61N 5/10* (2006.01)
*A61B 6/04* (2006.01)

(52) U.S. Cl.
CPC .......... *A61N 5/1084* (2013.01); *A61B 6/0407* (2013.01); *A61N 5/1045* (2013.01);
(Continued)

(58) Field of Classification Search
None
See application file for complete search history.

(56) References Cited

U.S. PATENT DOCUMENTS 6,937,693 B2 * 8/2005 Svatos .................. A61N 5/103
378/65
8,139,714 B1 * 3/2012 Sahadevan ............. A61N 5/025
378/65

(Continued)

FOREIGN PATENT DOCUMENTS

CN   101883608   11/2010
CN   108042931   5/2018
(Continued)

*Primary Examiner* — Hoon K Song
(74) *Attorney, Agent, or Firm* — Emerson, Thomson & Bennett, LLC; Roger D. Emerson; Warren A. Rosborough

(57) ABSTRACT

The present disclosure provides a radiation therapy device and system. The radiation therapy device includes a first treatment head and a second treatment head. A beam emitted from the second treatment head intersects with a beam emitted from the first treatment head at an intersection point. The first treatment head is an X-ray treatment head, and the second treatment head is an X-ray treatment head, a multi-source focusing treatment head, or an intensity-modulated treatment head. The radiation therapy device may increase a dose rate at the intersection point.

18 Claims, 6 Drawing Sheets

(52) U.S. Cl.
CPC ......... *A61N 5/1065* (2013.01); *A61N 5/1081* (2013.01); *A61N 2005/1085* (2013.01)

(56) References Cited

U.S. PATENT DOCUMENTS

| | | | |
|---|---|---|---|
| 8,591,107 B2 * | 11/2013 | Peters | A61B 6/4441 378/197 |
| 2009/0088625 A1 * | 4/2009 | Oosting | A61N 5/1084 600/425 |
| 2015/0251022 A1 * | 9/2015 | Liu | A61N 5/01 600/1 |
| 2016/0310763 A1 | 10/2016 | Grady et al. | |
| 2019/0175945 A1 * | 6/2019 | Yan | A61N 5/1084 |

FOREIGN PATENT DOCUMENTS

| | | |
|---|---|---|
| CN | 108175955 | 6/2018 |
| WO | 2014/166040 | 10/2014 |
| WO | 2015/062093 | 5/2015 |

\* cited by examiner

RADIATION THERAPY DEVICE AND SYSTEM

CROSS-REFERENCE TO RELATED APPLICATION

This application is a continuation of International Application No. PCT/CN2019/070849 filed on Jan. 8, 2019 and entitled "RADIATION THERAPY DEVICE AND SYSTEM". The International Application claims priority to Chinese Patent Application No. 201810037191.7, filed on Jan. 15, 2018 and entitled "RADIATION THERAPY SYSTEM". The entire disclosures of the prior applications are hereby incorporated by reference in their entirety.

TECHNICAL FIELD

The present disclosure relates to the field of medical appliance technologies, and more particularly, to a radiation therapy device and system.

BACKGROUND

Radiation therapy has become one of main means for treatment of malignant tumors. According to types of radioactive rays, mainstream radioactive rays include γ-ray radiation therapy devices and X-ray radiation therapy devices.

In the actual radiation therapy processes, no matter what type of radiation therapy devices are used, doctors usually hope that dose rates at tumor target regions are as high as possible. This is because the higher the dose rates at the tumor target regions are, the more successfully DNA chains of tumor cells can be destroyed, and the better the therapeutic effects are. The dose rates refer to doses applied to the tumor target regions in unit time.

SUMMARY

Embodiments of the present disclosure provide a radiation therapy device, which includes a first treatment head and a second treatment head. A beam emitted from the second treatment head intersects with a beam emitted from the first treatment head at an intersection point. The first treatment head is an X-ray treatment head configured to generate a single narrow X-ray beam, and the second treatment head is an X-ray treatment head, a multi-source focusing treatment head, or an intensity-modulated treatment head.

In an embodiment, the X-ray treatment head includes a channel collimator configured to limit a beam. The channel collimator includes a plurality of beam channels, and any two of the beam channels are different in at least one of aperture size and shape. Alternatively, the channel collimator includes a single beam channel, and the single beam channel is adjustable in at least one of shape and size.

In an embodiment, the X-ray treatment head further includes an accelerator configured to emit the beam.

In an embodiment, the X-ray treatment head further includes a multi-leaf collimator configured to conform the beam, and the multi-leaf collimator is connected to the channel collimator. The channel collimator is configured to limit the beam conformed by the multi-leaf collimator.

In an embodiment, the channel collimator is detachably connected to the multi-leaf collimator.

In an embodiment, the channel collimator is movable with respect to the multi-leaf collimator.

In an embodiment, at least one of the first treatment head and the second treatment head is arranged on a rotating gantry.

In an embodiment, at least one of the first treatment head and the second treatment head is reciprocally rotatable around a rotation axis of a rotating gantry or continuously rotatable through 360 degrees around the rotation axis of the rotating gantry.

In an embodiment, at least one of the first treatment head and the second treatment head is axially movable or swingable around the rotation axis of the rotating gantry.

In an embodiment, a radial angle formed between a beam centerline of the first treatment head and a beam centerline of the second treatment head is less than or equal to 180 degrees. The radial angle is an angle formed between an orthographic projection of the beam centerline of the first treatment head on a first section and an orthographic projection of the beam centerline of the second treatment head on the first section, and the first section is a section perpendicular to the rotation axis.

In an embodiment, an axial angle formed between a beam centerline of the first treatment head and a beam centerline of the second treatment head is less than or equal to 90 degrees. The axial angle is an angle formed between an orthographic projection of the beam centerline of the first treatment head on a second section and an orthographic projection of the beam centerline of the second treatment head on the second section, and the second section is a section parallel to or passing through the rotation axis.

In an embodiment, the radiation therapy device further includes a third treatment head. A beam emitted from the third treatment head intersects with the beam emitted from the first treatment head and the beam emitted from the second treatment head at the intersection point. The third treatment head is an X-ray treatment head, a multi-source focusing treatment head, or an intensity-modulated treatment head.

In an embodiment, the second treatment head is an X-ray treatment head, and the third treatment head is an X-ray treatment head.

In an embodiment, at least one of the first treatment head, the second treatment head and the third treatment head is arranged on the rotating gantry.

In an embodiment, at least one of the first treatment head, the second treatment head and the third treatment head is axially movable or swingable along the rotation axis of the rotating gantry.

In an embodiment, the first treatment head, the second treatment head and the third treatment head are arranged on a fixing apparatus, and the fixing apparatus is connected to the rotating gantry.

In an embodiment, a radial angle formed between two adjacent treatment heads ranges from 5 degrees to 45 degrees. The radial angle is an angle formed between orthographic projections of beam centerlines of the two adjacent treatment heads on a first section, and the first section is a section perpendicular to the rotation axis.

In an embodiment, the rotating gantry is a roller gantry or a C-shaped arm.

In an embodiment, the multi-source focusing treatment head emits an X-ray beam or a γ-ray beam, and the intensity-modulated treatment head emits an X-ray beam or a γ-ray beam.

The embodiments of the present disclosure provide a radiation therapy system, which includes a treatment couch and the aforementioned radiation therapy device.

BRIEF DESCRIPTION OF THE DRAWINGS

To describe the technical solutions of the embodiments of the present disclosure or that of the prior art more clearly, the accompanying drawings required for describing the embodiments or the prior art will be briefly introduced below. Apparently, the accompanying drawings in the following description are merely some embodiments of the present disclosure. For the skilled in the art, other accompanying drawings may also be derived from these accompanying drawings without creative efforts.

DETAILED DESCRIPTION

Detailed description of the present disclosure is further made below with reference to drawings and embodiments to make the objects, technical solutions and advantages of the present disclosure more apparent. It is to be understood that the specific embodiments described herein are only intended to explain the present disclosure, and are not restrictive of the present disclosure.

At present, cobalt-60 (Co-60) is radioactive and has higher requirements for shielding properties of γ-ray radiation therapy devices. Therefore, the shielding properties of the γ-ray radiation therapy devices need to be strengthened and masses of treatment heads are increased if more radiation sources are employed to increase the dose rate, which is disadvantageous to implementation of rotary focusing of the treatment heads. For X-ray radiation therapy devices, physicians generally need to increase the dose rate through repeated or longer-term radiation, which is prone to having a negative effect on the accuracy of the radiation therapy.

Figure 1:
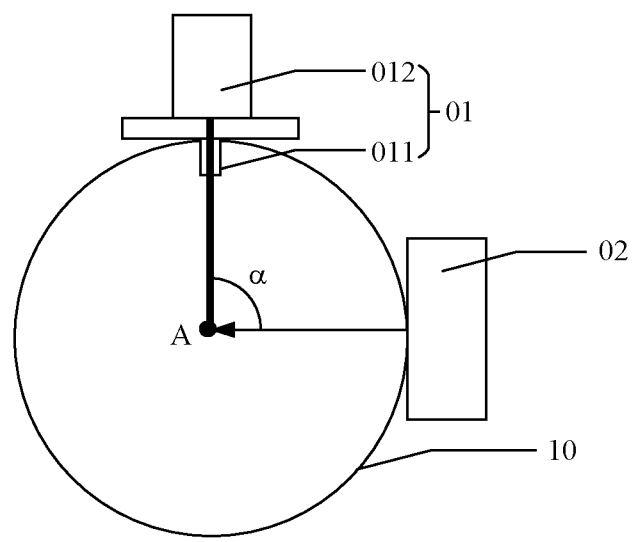
FIG. 1 is a schematic structural diagram of a radiation therapy device according to an embodiment of the present disclosure.

FIG. 1 is a schematic structural diagram of a radiation therapy device according to an embodiment of the present disclosure. As shown in FIG. 1, the radiation therapy device includes a first treatment head 01 and a second treatment head 02. A beam emitted from the first treatment head 01 intersects with a beam emitted from the second treatment head 02 at an intersection point A. The first treatment head 01 is an X-ray treatment head, and the second treatment head 02 is a multi-source focusing treatment head, an X-ray treatment head, or an intensity-modulated treatment head.

As one of accelerator treatment heads, the X-ray treatment head is configured to generate a single narrow X-ray beam. The multi-source focusing treatment head is a treatment head including a plurality of radiation sources, and beams emitted from the plurality of radiation sources may be focused on one point. As a treatment head based on intensity modulated radiation therapy (IMRT) technologies, the intensity-modulated treatment head can emit a beam whose shape of radiation field may be adjusted according to a shape of an affected target region.

In the embodiments of the present disclosure, no matter what type of treatment head the second treatment head 02 is, the beam emitted from the second treatment head 02 may intersect with the beam emitted from the first treatment head 01 at an intersection point, and a dose rate at the intersection point A is the sum of the dose rate of the first treatment head 01 and the dose rate of the second treatment head 02. Compared with radiation therapy using a single treatment head, the dose rate at the intersection point A may increase significantly. In addition, the first treatment head 01 is an X-ray treatment head, which uses electron beam shooting to emit X-rays. Therefore, the first treatment head 01 does not have a bulky shielding structure, and is lighter in weight than the multi-source focusing treatment head, such that it is avoidable that the treatment head of the radiation therapy device is overmassive, and it is ensured that the treatment head may rotate normally.

When the radiation therapy device is used for tumor treatment, a to-be-treated target spot or target region may be overlapped with the intersection point A to implement high-dose radiation therapy.

In an embodiment, as shown in FIG. 1, the X-ray treatment head 01 includes a channel collimator 011 configured to limit a beam and an accelerator 012 configured to emit an X-ray beam. The channel collimator 011 may limit the X-ray beam emitted from the accelerator 012 to a single narrow beam. For example, the single narrow beam has a diameter of about 6 mm to 60 mm. Of course, the diameter of the single narrow beam may be preset according to specific needs, which is not specifically limited in the embodiments of the present disclosure.

Figure 2:
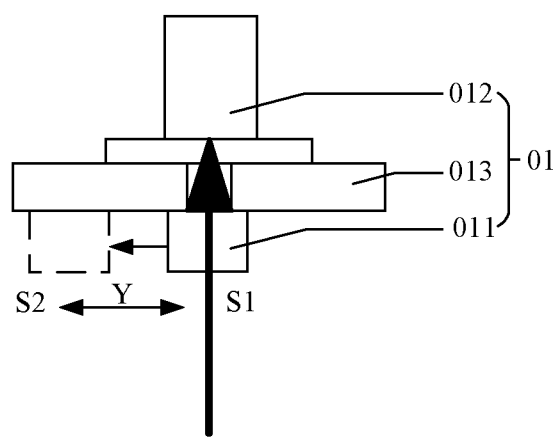
FIG. 2 is a schematic structural diagram of an X-ray treatment head according to an embodiment of the present disclosure.

In another embodiment, as shown in FIG. 2, the X-ray treatment head 01 includes an accelerator 012, a channel collimator 011 configured to limit the beam, and a multi-leaf collimator (MLC) 013 positioned between the accelerator 012 and the channel collimator 011. The MLC 013 is configured to conform the X-ray beam emitted from the accelerator 012, and the channel collimator 011 is configured to limit the X-ray beam conformed by the MLC 013. That is, the MLC 013 elementarily conforms (i.e., primary conform) the X-ray beam, and the channel collimator 011 further conforms (i.e., secondary conform) the X-ray beam, such that the conformed X-ray beam is limited to the single narrow beam.

Further, the channel collimator 011 may be detachably connected to the MLC 013. For example, the channel collimator 011 may be clamped to or connected to the MLC 013 through bolts.

Alternatively, the channel collimator 011 also may be movable with respect to the MLC 013. For example, on the MLC 013 there is provided with a rail groove, and on the channel collimator 011 there is provided with a slider, which may be snapped into the rail groove and can slide in the rail groove.

As shown in FIG. 2, the channel collimator 011 may move with respect to the MLC 013 in a direction (for example, the Y direction as shown in FIG. 2) perpendicular to the beam emitted from the accelerator 012. When the channel collimator 011 moves from a position S1 to a position S2, the channel collimator 011 is positioned in a region other than the region through which the X-ray beam conformed by the MLC 013 passes. At this moment, the first treatment head 01 conforms the X-ray beam through the MLC 013, and the first treatment head 01 is similar to an ordinary intensity-modulated treatment head, and intensity modulated radiation therapy may be implemented. When the channel collimator 011 moves from the position S2 to the position S1, the channel collimator 011 is positioned in the region through which the X-ray beam conformed by the MLC 013 passes. At this moment, the channel collimator 011 of the first treatment head 01 limits the X-ray beam conformed by the MLC 013 to the single narrow beam. Thus, the first treatment head 01 may adjust different forms of radiation therapy as needed.

Figure 3:
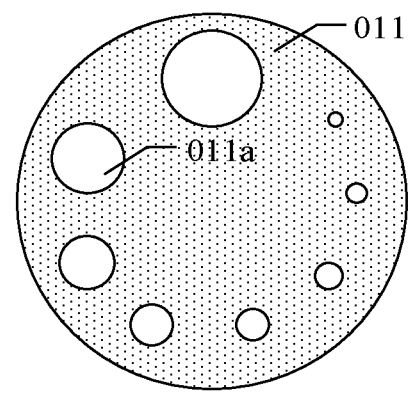
FIG. 3 is a schematic structural diagram of a channel collimator according to an embodiment of the present disclosure.

Alternatively, as shown in FIG. 3, the channel collimator 011 in the foregoing embodiments may include a plurality of beam channels 011*a*. Any two of the plurality of beam channels 011*a* are different in at least one of aperture size and shape. For example, in the structure as shown in FIG. 3, the channel collimator 011 includes eight beam channels 011*a* having different aperture size.

Figure 4:
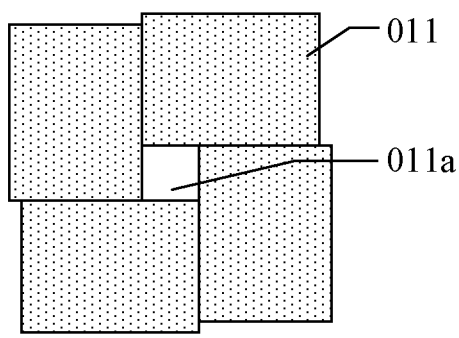
FIG. 4 and FIG. 5 are schematic structural diagrams of another channel collimator according to an embodiment of the present disclosure.
Figure 5:
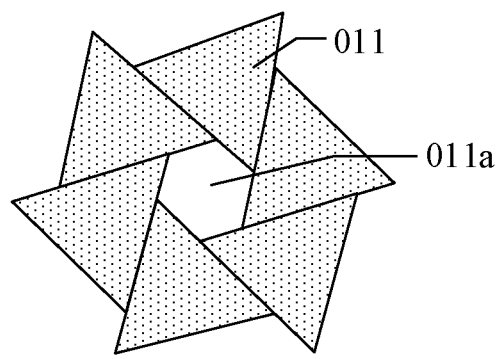

Alternatively, as shown in FIG. 4 and FIG. 5, the channel collimator 011 may also include a single beam channel 011*a* which is adjustable in at least one of shape and size. For example, the shape of the beam channel 011*a* may be adjustable. For example, the shape of the beam channel 011*a* may be adjusted from a rectangle as shown in FIG. 4 to a hexagon as shown in FIG. 5. The size of the beam channel 011*a* also may be adjustable. For example, referring to FIG. 4 and FIG. 5, the channel collimator 011 may include a plurality of collimation blocks, the plurality of collimation blocks enclose the beam channel 011*a*, and a relative position between every two adjacent collimation blocks are adjustable. Thus, the size of the collimation channel may be changed by adjusting the position of the collimation block in the channel collimator 011. Of course, the shape and the size of the collimation channel 011*a* also may be simultaneously adjusted, which is not specifically limited here.

Figure 6:
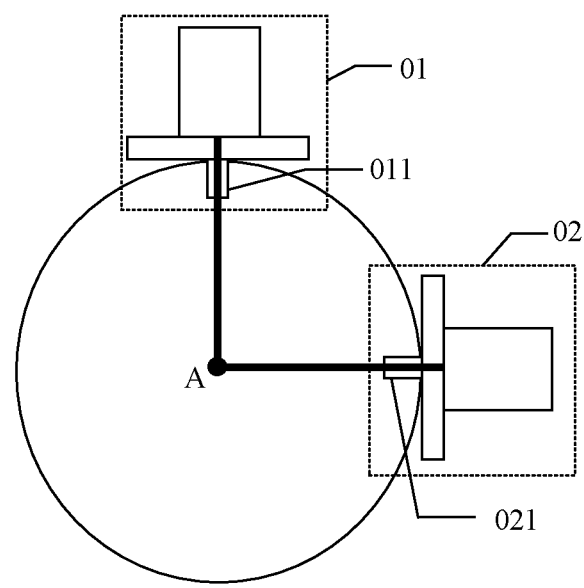
FIG. 6 is a schematic structural diagram of the radiation therapy device when a second treatment head is the X-ray treatment head that is configured to cause a second beam to emit from the second treatment head through a second single beam channel, according to an embodiment of the present disclosure.

In the case where both the first treatment head 01 and the second treatment head 02 are the X-ray treatment heads, in an embodiment, as shown in FIG. 6, the X-ray beams emitted from the accelerator in each treatment head 01 are respectively limited by the channel collimator to form a single narrow beam. The single narrow beam has a diameter of about 6 mm to 10 mm. The beam emitted from the first treatment head 01 intersects with the beam emitted from the second treatment head 02 at an intersection point A, and a dose rate at the intersection point A may be the sum of the dose rates of the X-ray beams emitted from the two X-ray treatment heads. Generally, one X-ray treatment head may emit an X-ray beam of 1400 MU/Min, whose dose rate is about 3.5 Gy/Min. In such a case, the dose rate at the intersection point may come up to 7 Gy/Min, such that the dose rate at the intersection point is greatly increased, and thus requirements for a higher clinical dose rate are met.

It is also to be noted here that the multi-source focusing treatment head may focus a plurality of beams on the intersection point A, and the plurality of beams are X-ray beams or γ-ray beams.

Figure 7:
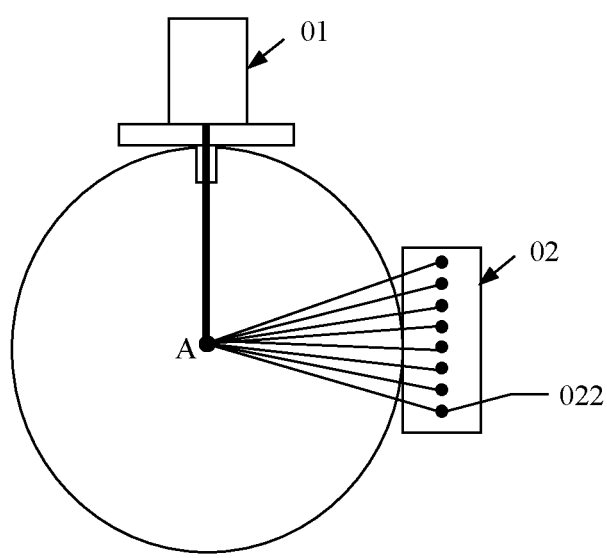
FIG. 7 is a schematic structural diagram of the radiation therapy device when the second treatment head is a multi-source focusing treatment head according to an embodiment of the present disclosure.

When the second treatment head 02 is the multi-source focusing treatment head and the multi-source focusing treatment head emits the γ-ray beam, as shown in FIG. 7, the multi-source focusing treatment head 02 may include a plurality of Cobalt-60 radiation sources 022. The γ-ray beams emitted from the plurality of Cobalt-60 radiation sources 022 are focused on the intersection point A through a collimator (not shown in FIG. 7). When the multi-source focusing treatment head 02 emits the X-ray beam, the multi-source focusing treatment head 02 may include an accelerator and the X-ray beam emitted from the accelerator is focused on the intersection point through the collimator.

The beams emitted from the multi-source focusing treatment head and the X-ray treatment head are both approximately circular at the intersection point, and thus the multi-source focusing treatment head and the X-ray treatment head may cooperate with each other to perform fill-in radiation therapy on a target region. The fill-in radiation therapy may provide a high-dose radiation for tumor tissues, but surrounding tissues are subjected to less damage from the radiation. Therefore, precise treatment characteristics of the fill-in radiation therapy have a good therapeutic effect on intracranial tumors or smaller tumors at head and neck. The expression "the beams are both approximately circular at the intersection point" may refer to a fact that orthographic projections of the beams emitted from the treatment heads on a first plane are approximately circular, wherein the first plane is a plane perpendicular to the beam centerline.

Taking an example where the second treatment head 02 is the multi-source focusing treatment head that emits the γ-ray beam, the dose rate of the second treatment head 02 may come up to 3 Gy/Min. The X-ray beam emitted from the X-ray treatment head may come up to 1,400 MU/Min, and the dose rate of the X-ray treatment head is about 3.5 Gy/Min. When the multi-source focusing treatment head 02 and the X-ray treatment head 01 perform the fill-in radiation therapy, as shown in FIG. 7, the beams emitted from the two treatment heads intersect at the intersection point A, and the dose rate at the intersection point A is the sum of the dose rates of the two treatment heads, which may come up to 6.5 Gy/Min. Therefore, the dose rate at the intersection A is greatly increased, requirements for a higher clinical dose rate are met, and accurate fill-in radiation therapy of the target region is implemented.

Figure 8:
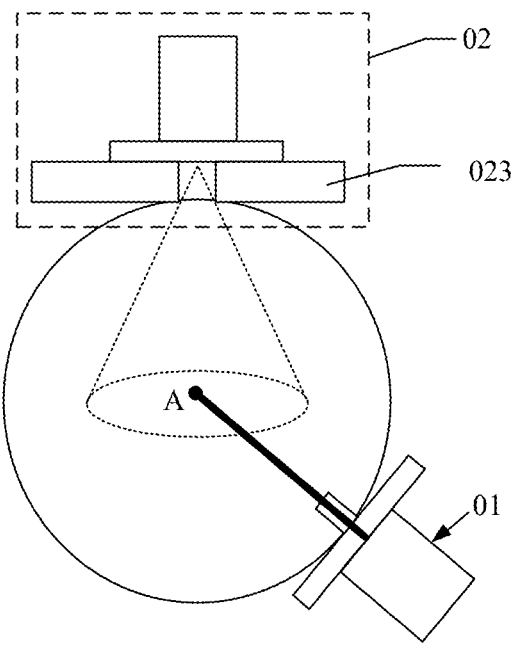
FIG. 8 is a schematic structural diagram of the radiation therapy device when the second treatment head is an intensity-modulated treatment head according to an embodiment of the present disclosure.

It is also to be noted here that when the second treatment head 02 is the intensity-modulated treatment head, referring to FIG. 8, the intensity-modulated treatment head 02 may include an MLC 023 that can conform the beam, which is the X-ray beam or the γ-ray beam. A beam-transmissive region (also referred to as a radiation field) consistent with the shape of a tumor may be formed by using the MLC 023, and the beam transmits through this region and radiates the tumor tissues, which is generally suitable for the treatment of larger body tumors. As shown in FIG. 8, the beam emitted from the X-ray treatment head 01 intersects with a conformal region of the intensity-modulated treatment head 02 at the intersection point A, and the dose rate at the intersection point A is increased.

For another example as shown in FIG. 1, the radiation therapy device may further include a rotating gantry 10, and the first treatment head 01 and the second treatment head 02 may be arranged on the rotating gantry 10, such that the rotating gantry 10 may drive the first treatment head 01 and the second treatment head 02 to rotate around a rotation axis of the rotating gantry 10.

Of course, one of the first treatment head 01 and the second treatment head 02 may be arranged on the rotating gantry 10, while the other one may be arranged at other position such as a fixed gantry. The embodiments of the present disclosure are not specifically limited thereto.

The first treatment head 01 and the second treatment head 02 may have various movement modes. At least one of the first treatment head 01 and the second treatment head 02 may reciprocally rotate around the rotation axis of the rotating gantry 10 or continuously rotate 360 degrees around the rotation axis of the rotating gantry 10. Alternatively, at least one of the first treatment head 01 and the second treatment head 02 may axially move or swing along the rotation axis of the rotating gantry. The expression "reciprocally rotate" may refer to rotating a certain angle in a certain direction (for example, a clockwise direction) and then rotating a certain angle in a reverse direction (for example, a counterclockwise direction).

Through these motion modes, non-coplanar radiation of a tumor target region or target spot may be implemented (that is, the tumor target region or target spot is radiated from different directions). Thus, through the technical solution of the embodiments of the present disclosure, the dose rate at the tumor target region may be increased, while damage to normal tissues may be reduced.

Alternatively, the axial movement or swinging of at least one of the first treatment head 01 and the second treatment head 02 along the rotation axis of the rotating gantry includes: at least one of the first treatment head 01 and the second treatment head 02 itself axially moving or swinging along the rotation axis of the rotating gantry, or the rotating gantry itself reciprocally rotating or swinging around a preset axis such that at least one of the first treatment head 01 and the second treatment head 02 is driven to axially move or swing along the rotation axis. The preset axis may be parallel to the rotation axis or may be the rotation axis, or the preset axis may intersect with the rotation axis.

Alternatively, the axial movement or swinging of at least one of the first treatment head 01 and the second treatment head 02 along the rotation axis of the rotating gantry includes: at least one of the first treatment head 01 and the second treatment head 02 making an arc motion or a rectilinear motion along the rotation axis of the rotating gantry, or at least one of the first treatment head 01 and the second treatment head 02 axially swinging along the rotation axis of the rotating gantry with itself as a pivotal axis.

For example, the rotating gantry 10 may be provided with an arc-shaped guide rail groove or a linear guide rail groove extending along the axial direction of the rotation axis of the rotating gantry, and at least one of the first treatment head 01 and the second treatment head 02 is connected to a slider, which is clamped in the guide groove and can slide in the guide groove. Thereby, the treatment head can make the arc motion or rectilinear motion around the rotation axis of the rotating gantry.

Alternatively, a connecting shaft is fixed to the rotating gantry, the connecting shaft is perpendicular to the rotation axis of the rotating gantry, and the treatment head may be rotatably connected to the connecting shaft and can rotate around the connecting shaft. Thereby, the treatment head can axially swing along the rotation axis of the rotating gantry with itself as the pivotal axis, as shown with the arrow in FIG. 9.

In the embodiments of the present disclosure, the rotating gantry may be a roller gantry, a C-shaped arm, or a drum-shaped gantry, but the embodiments of the present disclosure are not specifically limited thereto.

Positional relationships between the first treatment head 01 and the second treatment head 02 may also be various. A radial angle formed between a beam centerline of the first treatment head 01 and a beam centerline of the second treatment head 02 may be less than or equal to 180 degrees, and an axial angle formed between a beam centerline of the first treatment head 01 and a beam centerline of the second treatment head 02 may be less than or equal to 90 degrees.

As shown in FIG. 1, from the perspective of a section (i.e., the section perpendicular to the rotation axis) in the direction of the rotation axis (the intersection point A is on the rotation axis) of the rotating gantry, the angle formed between the beam centerline of the first treatment head 01 and the beam centerline of the second treatment head 02 is α. That is, the radial angle α is less than or equal to 180 degrees. For example, the radial angle α is 30 degrees, 45 degrees, 60 degrees, 75 degrees, 90 degrees, 105 degrees, 120 degrees, 135 degrees, 150 degrees, 165 degrees, or 180 degrees. As can be seen from FIG. 1, the radial angle may be an angle formed between an orthographic projection of the beam centerline of the first treatment head 01 on a first section and an orthographic projection of the beam centerline of the second treatment head 02 on the first section, and the first section is a section perpendicular to the rotation axis.

For example, the radial angle α also may be less than or equal to 30 degrees, less than or equal to 45 degrees, less than or equal to 60 degrees, less than or equal to 75 degrees, less than or equal to 90 degrees, less than or equal to 105 degrees, less than or equal to 120 degrees, less than or equal to 135 degrees, less than or equal to 150 degrees, or less than or equal to 165 degrees, etc.

Figure 9:
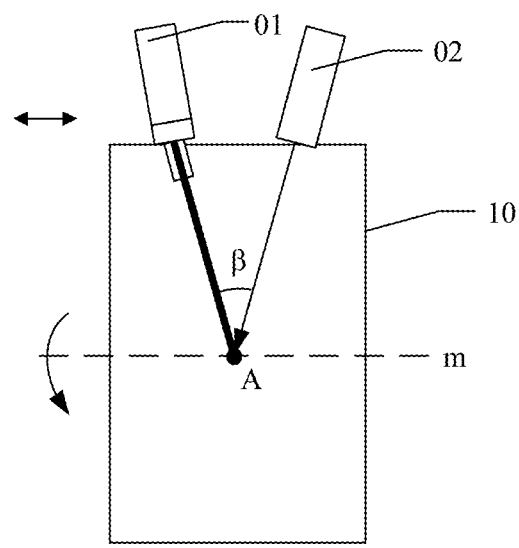
FIG. 9 is a schematic diagram of an axial angle formed between a beam centerline of a first treatment head and a beam centerline of the second treatment head according to an embodiment of the present disclosure.

As shown in FIG. 9, from the perspective of a section (i.e., the section where the rotation axis m is) of the rotation axis m penetrating through the rotating gantry 10, the angle formed between the beam centerline of the first treatment head 01 and the beam centerline of the second treatment head 02 is β. That is, the axial angle β is less than or equal to 90 degrees. For example, the axial angle β is 30 degrees, 45 degrees, 60 degrees, 75 degrees, or 90 degrees. As can be seen from FIG. 9, the axial angle may be an angle formed between an orthographic projection of the beam centerline of the first treatment head 01 on a second section and an orthographic projection of the beam centerline of the second treatment head 02 on the second section, and the second section is a section passing through the rotation axis m.

Figure 10:
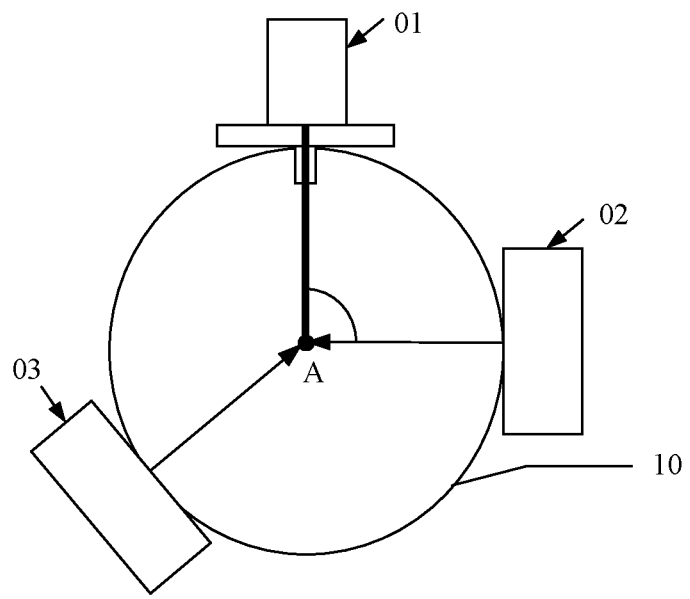
FIG. 10 illustrates a radiation therapy device including a third treatment head according to an embodiment of the present disclosure.

As shown in FIG. 10, the radiation therapy device may further include a third treatment head 03, and a beam emitted from the third treatment head 03 intersects with the beam emitted from the first treatment head 01 and the beam emitted from the second treatment head 02 at the intersection point A. The third treatment head 03 may be an X-ray treatment head, a multi-source focusing treatment head, or an intensity-modulated treatment head. In this way, the dose rate at the intersection point A may be further increased.

Figure 11:
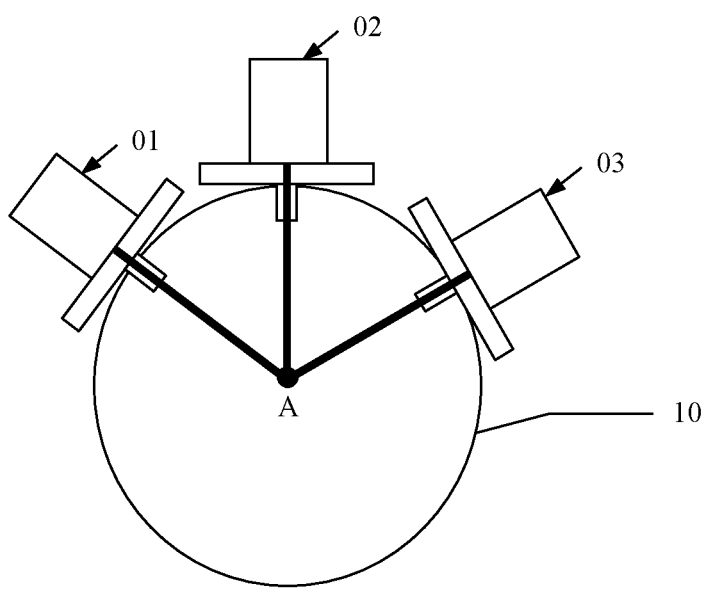
FIG. 11 is a schematic structural diagram of the radiation therapy device when the second treatment head and the third treatment head are the X-ray treatment heads that are configured to cause a second beam and a third beam to emit from the second treatment head and the third treatment head respectively through a second single beam channel and a third single beam channel, according to an embodiment of the present disclosure.

In an embodiment, as shown in FIG. 11, the first treatment head 01, the second treatment head 02 and the third treatment head 03 are all X-ray treatment heads, and beams emitted from the three X-ray treatment heads intersect at the intersection point A.

The third treatment head 03 may be arranged on the rotating gantry 10 like any one of the first treatment head 01 or the second treatment head 02, or may be arranged in other positions as required.

If the third treatment head 03 is arranged on the rotating gantry 10, the rotating gantry 10 may also drive the third treatment head 03 to rotate around the rotation axis of the rotating gantry 10. Likewise, the third treatment head 03 may also have various movement modes. The third treatment head 03 may reciprocally rotate around the rotation axis or continuously rotate 360 degrees around the rotation axis, or the third treatment head 03 may axially move or swing along the rotation axis of the rotating gantry.

Through these motion modes, non-coplanar radiation of a to-be-treated target region or target spot may be implemented by interworking between the first treatment head 01 and the second treatment head 02. Thus, through the technical solution of the embodiments of the present disclosure, the dose rate at the tumor target region may be increased, while damage to normal tissues may be reduced.

Figure 12:
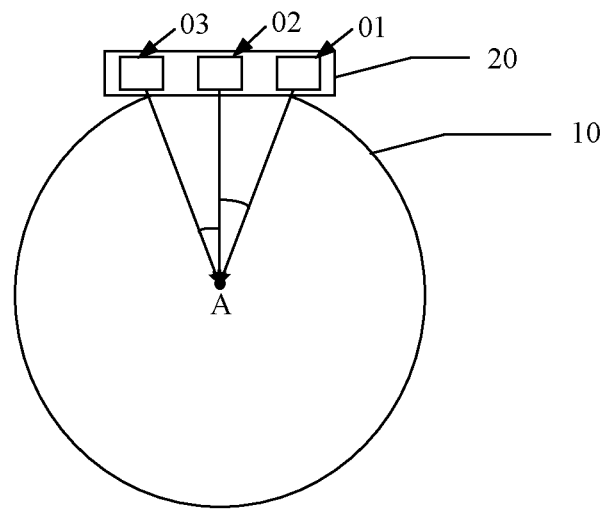
FIG. 12 is a schematic structural diagram of the radiation therapy device when the first treatment head, the second treatment head and the third treatment head are arranged on a fixing apparatus according to an embodiment of the present disclosure.

In another embodiment, as shown in FIG. 12, the first treatment head 01, the second treatment head 02 and the third treatment head 03 are arranged on a fixing apparatus 20, and the fixing apparatus 20 is connected to the rotating gantry 10.

Alternatively, as shown in FIG. 12, among the first treatment head 01, the second treatment head 02 and the third treatment head 03, the radial angle formed between two adjacent treatment heads ranges from 5 degrees to 45 degrees. That is, from the perspective of the section in the direction of the rotation axis (the intersection point is on the rotation axis) of the rotating gantry, among the first treatment head 01, the second treatment head 02 and the third treatment head 03, the angle formed between the beam centerlines of two adjacent treatment heads ranges from 5 degrees to 45 degrees, i.e., the radial angle ranges from 5 degrees to 45 degrees. For example, the radial angle is 5 degrees, 10 degrees, 15 degrees, 20 degrees, 25 degrees, 30 degrees, or 45 degrees.

Of course, the radiation therapy device may further include a fourth treatment head, a fifth treatment head, . . . , and an $N^{th}$ treatment head (N is an integer greater than 3), which is not specifically limited in the embodiments of the present disclosure. In addition, the larger the number of the treatment heads included in the radiation therapy device, the smaller the radial angle formed between two adjacent treatment heads.

It is to be noted here that the radial angle formed between the two adjacent treatment heads may be equal or may be unequal.

Here, the fourth treatment head, the fifth treatment head, . . . , and the $N^{th}$ treatment head may all be the X-ray treatment heads.

Figure 13:
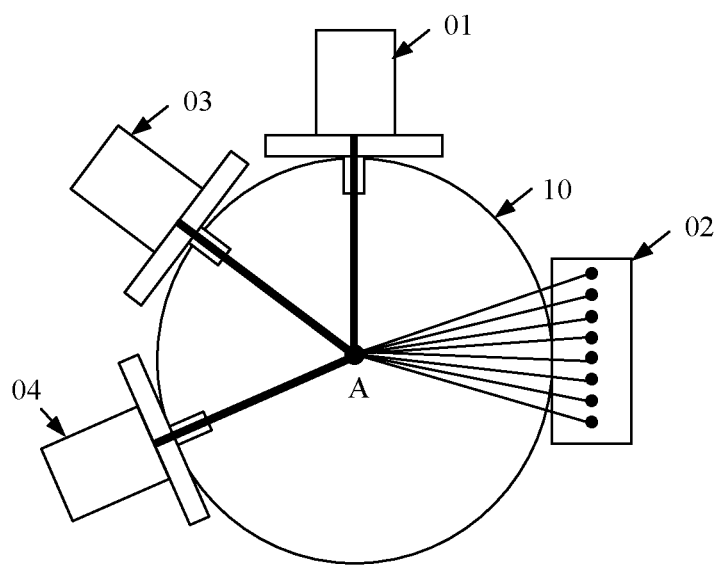
FIG. 13 is a schematic structural diagram of the radiation therapy device when the first treatment head is the X-ray treatment head configured to cause a first beam to emit from the first treatment head through a first single beam channel, the second treatment head is the multi-source focusing treatment head, and the third treatment head and a fourth treatment head are the X-ray treatment heads that are configured to cause a third beam and a fourth beam to emit from the third treatment head and the fourth treatment head respectively through a third single beam channel and a fourth single beam channel, according to an embodiment of the present disclosure.

For example, as shown in FIG. 13, the first treatment head 01 is the X-ray treatment head, the second treatment head 02 is the multi-source focusing treatment head, and both the third treatment head 03 and the fourth treatment head 04 are the X-ray treatment heads. Furthermore, when the rotating gantry 10 is the roller gantry, positions of the X-ray treatment heads (i.e., the first treatment head 01, the third treatment head 03, and the fourth treatment head 04) on the roller gantry 10 may be adjusted to reach mass balance with the multi-source focusing treatment head 02, so as to facilitate the rotation of the rotating gantry 10.

The present disclosure further provides a radiation therapy system, which may include a treatment couch and a radiation therapy device. The radiation therapy device may be the radiation therapy device provided by any one of the preceding embodiments of the present disclosure, for example, any one of the radiation therapy devices as shown in FIG. 1 to FIG. 13.

It is to be noted that the term "and/or" in the embodiments of the present disclosure is merely used for describing an association relationship between association objects represents presence of three relationships. For example, A and/or B may represent presence of the A only, presence of both the A and the B, and presence of the B only. Moreover, Character "/" generally indicates that an "or" relationship is between the association objects.

The above are implementations disclosed by the present disclosure. However, the described contents are merely implementations adopted for better understanding the present disclosure rather than limiting the present disclosure. Any person skilled in the art can make any modification and variation to the implementing forms or details without departing from the spirit and scope of the present disclosure. However, the patent protection scope of the present disclosure should still be subjected to the scope defined in the appended claims.

What is claimed is:

1. A radiation therapy device, comprising a plurality of treatment heads and a rotating gantry, wherein
the plurality of treatment heads includes an X-ray treatment head as a first treatment head and a second treatment head, the first treatment head is configured to cause a first beam to emit from the first treatment head through a first single beam channel; and
the plurality of treatment heads are configured in a manner that beams emitted from the plurality of treatment heads intersect at an intersection point such that a dose rate of the beams at the intersection point is increased for relatively high-dose radiation therapy compared to the dose rate of each of the beams,
wherein an angle between an orthographic projection of a beam centerline of the first treatment head on a first section and an orthographic projection of a beam centerline of the second treatment head on the first section is less than or equal to 180 degrees, and the first section is a section perpendicular to the rotation axis, and
an angle between an orthographic projection of the beam centerline of the first treatment head on a second section and an orthographic projection of the beam centerline of the second treatment head on the second section is greater than 0 degree and less than or equal to 90 degrees, and the second section is a section passing through the rotation axis.

2. The radiation therapy device according to claim 1, wherein the plurality of treatment heads are of different types of radiation therapy treatment heads.

3. The radiation therapy device according to claim 1, wherein the second treatment head is an X-ray treatment head that is configured to cause a second beam to emit from the second treatment head through a second single beam channel.

4. The radiation therapy device according to claim 3, wherein the X-ray treatment head comprises a channel collimator configured to limit a beam generated by the X-ray treatment head; wherein the channel collimator comprises:
 a plurality of beam channels, wherein any two of the beam channels are different in at least one of aperture size and shape; or
 a single beam channel, and the single beam channel is adjustable in at least one of shape and size.

5. The radiation therapy device according to claim 4, wherein the X-ray treatment head further comprises an accelerator configured to emit the beam.

6. The radiation therapy device according to claim 4, wherein the X-ray treatment head further comprises a multi-leaf collimator configured to conform the beam, and the multi-leaf collimator is connected to the channel collimator; and
 wherein the channel collimator is configured to limit the beam conformed by the multi-leaf collimator.

7. The radiation therapy device according to claim 6, wherein the channel collimator is detachably connected to the multi-leaf collimator.

8. The radiation therapy device according to claim 6, wherein the channel collimator is movable with respect to the multi-leaf collimator.

9. The radiation therapy device according to claim 3, wherein at least one of the first treatment head and the second treatment head is arranged on the rotating gantry and rotatable around the rotation axis of the rotating gantry.

10. The radiation therapy device according to claim 3, wherein at least one of the first treatment head and the second treatment head is reciprocally rotatable around the rotation axis of the rotating gantry or continuously rotatable through 360 degrees around the rotation axis of the rotating gantry.

11. The radiation therapy device according to claim 3, wherein at least one of the first treatment head and the second treatment head is axially movable or swingable along the rotation axis of the rotating gantry.

12. The radiation therapy device according to claim 3, further comprising:
 a third treatment head, a beam emitted from the third treatment head intersecting with the beam emitted from the first treatment head and the beam emitted from the second treatment head at the intersection point.

13. The radiation therapy device according to claim 12, the third treatment head is an X-ray treatment head that is configured to cause a third beam to emit from the third treatment head through a third single beam channel.

14. The radiation therapy device according to claim 12, wherein at least one of the first treatment head, the second treatment head and the third treatment head is arranged on the rotating gantry.

15. The radiation therapy device according to claim 14, wherein at least one of the first treatment head, the second treatment head and the third treatment head is axially movable or swingable along the rotation axis of the rotating gantry.

16. The radiation therapy device according to claim 9, wherein the rotating gantry is a roller gantry or a C-shaped arm.

17. A radiation therapy system, comprising: a treatment couch and a radiation therapy device; the radiation therapy device comprising a plurality of treatment heads and a rotating gantry, wherein
 the plurality of treatment heads comprise an X-ray treatment head as a first treatment head and a second treatment head, the first treatment head is configured to cause a first beam to emit from the first treatment head through a first single beam channel; and
 the plurality of treatment heads are configured in a manner that beams emitted from the plurality of treatment heads intersect at an intersection point such that a dose rate of the beams at the intersection point is increased for relatively high-dose radiation therapy compared to the dose rate of each of the beams,
 wherein an angle between an orthographic projection of a beam centerline of the first treatment head on a first section and an orthographic projection of a beam centerline of the second treatment head on the first section is less than or equal to 180 degrees, and the first section is a section perpendicular to the rotation axis, and
 an angle between an orthographic projection of the beam centerline of the first treatment head on a second section and an orthographic projection of the beam centerline of the second treatment head on the second section is greater than 0 degree and less than or equal to 90 degrees, and the second section is a section passing through the rotation axis.

18. The radiation therapy device according to claim 1, further comprising a fixed gantry, wherein one of the first treatment head and the second treatment head is arranged on the rotating gantry, and the other one of the first treatment head and the second treatment head is arranged on the fixed gantry.

* * * * *